(12) United States Patent
Chung et al.

(10) Patent No.: US 10,477,940 B2
(45) Date of Patent: Nov. 19, 2019

(54) FOLDER TYPE COSMETIC CONTAINER

(71) Applicant: CTK COSMETICS CO., LTD., Seongnam-si, Gyeonggi-do (KR)

(72) Inventors: In Yong Chung, Seoul (KR); Won Geun Go, Incheon (KR); Choung Gil Ok, Incheon (KR); Jae Hui Lee, Suwon-si (KR)

(73) Assignee: CTK COSMETICS CO., LTD., Seongnam-si (KR)

( * ) Notice: Subject to any disclaimer, the term of this patent is extended or adjusted under 35 U.S.C. 154(b) by 6 days.

(21) Appl. No.: 15/750,504

(22) PCT Filed: Dec. 15, 2017

(86) PCT No.: PCT/KR2017/014853
§ 371 (c)(1),
(2) Date: Feb. 6, 2018

(87) PCT Pub. No.: WO2019/022315
PCT Pub. Date: Jan. 31, 2019

(65) Prior Publication Data
US 2019/0029393 A1 Jan. 31, 2019

(30) Foreign Application Priority Data

Jul. 25, 2017 (KR) .......................... 10-2017-0093968

(51) Int. Cl.
*A45D 34/00* (2006.01)
(52) U.S. Cl.
CPC ........ *A45D 34/00* (2013.01); *A45D 2200/054* (2013.01)

(58) Field of Classification Search
CPC .. A45D 34/00; A45D 34/04; A45D 2034/005; A45D 40/22; A45D 2200/054; B65D 47/20; B65D 47/2018; G01F 11/30; G01F 11/32; G01F 11/286; G01F 11/288
USPC ............ 222/95–96, 105, 107, 162–163, 160, 222/167–168, 608, 207, 209, 212–213, 222/182–183, 630–633, 325–327, 477
See application file for complete search history.

(56) References Cited

U.S. PATENT DOCUMENTS

| 3,146,923 A * | 9/1964 | Chappell ............... G01F 11/263 222/477 |
| 3,405,843 A * | 10/1968 | Watson, Jr. ......... B05B 11/3001 222/95 |
| 3,741,439 A * | 6/1973 | Vehrs .................... B65D 35/40 222/103 |

(Continued)

FOREIGN PATENT DOCUMENTS

KR 10-2013-0115670 A 10/2013

*Primary Examiner* — Paul R Durand
*Assistant Examiner* — Andrew P Bainbridge
(74) *Attorney, Agent, or Firm* — Novick, Kim & Lee, PLLC; Jae Youn Kim (57) ABSTRACT

The present invention relates to a folder type cosmetic container that can reduce waste of content in the container by dispensing a predetermined amount of the content when the content is pressed by a pressing-dispensing member, so it can be conveniently used. Further, the folder type cosmetic container can improve productivity, reduce the manufacturing cost, and improve convenience in use by employing a simple structure for dispensing a predetermined amount of content.

10 Claims, 7 Drawing Sheets

(56) References Cited

U.S. PATENT DOCUMENTS

| | | | | |
|---|---|---|---|---|
| 4,728,011 A * | 3/1988 | Schuster | G01F 11/263 | 222/439 |
| 4,778,085 A * | 10/1988 | Bush | A47K 5/1215 | 222/207 |
| 4,949,875 A * | 8/1990 | Kuo | A46B 11/0006 | 222/156 |
| 5,105,984 A * | 4/1992 | Kazimir | B65D 35/28 | 222/103 |
| 5,487,489 A * | 1/1996 | Weiss | B05B 11/3056 | 222/1 |
| 5,518,051 A * | 5/1996 | Wells | A47K 5/00 | 141/114 |
| 6,247,621 B1 * | 6/2001 | Lewis | A47K 5/12 | 222/153.13 |
| 6,276,572 B1 * | 8/2001 | Evans | B65D 1/023 | 222/424.5 |
| 6,305,580 B1 * | 10/2001 | Chen | B05B 11/3056 | 222/162 |
| 6,343,723 B1 * | 2/2002 | Hickerson | G01F 11/263 | 222/442 |
| 6,695,174 B2 * | 2/2004 | Sørensen | A47K 5/1211 | 222/183 |
| 6,997,358 B2 * | 2/2006 | Wass | G01F 11/263 | 224/438 |
| 8,061,918 B2 * | 11/2011 | Skalitzky | A45D 34/00 | 222/146.5 |
| 8,646,658 B2 * | 2/2014 | Bae | A45D 34/02 | 222/182 |
| 2006/0186140 A1 * | 8/2006 | Kanfer | A45D 34/04 | 222/207 |
| 2008/0149098 A1 * | 6/2008 | Bonney | B05B 11/3056 | 128/200.22 |
| 2014/0008398 A1 * | 1/2014 | Law | G01F 11/263 | 222/477 |
| 2017/0029177 A1 * | 2/2017 | Holroyd | B65D 47/2018 | |

* cited by examiner

FOLDER TYPE COSMETIC CONTAINER

TECHNICAL FIELD

The present invention relates to a folder type cosmetic container that can reduce waste of content in the container by dispensing a predetermined amount of the content when the content is pressed by a pressing-dispensing member.

BACKGROUND ART

Cosmetics products are generally in various kinds, but are generally used by women to make themselves up. Cosmetics are usually classified into base makeup cosmetics using power, foundation, blusher, etc., and point makeup cosmetics using eyeshadow, mascara, and lip gloss. Such point makeup cosmetics are recently provided in a liquid state having higher viscosity that those of common liquid cosmetics.

The liquid-state cosmetics are usually packed and provided in forms of tube or bottle so that users can pour or squeeze the makeup in use, and users depend on their sense to squeeze an appropriate amount of makeup. However, since users press different portions of cosmetics, they have difficulty in squeezing a desired amount of makeup in use.

In order to solve this problem, a button type lib gloss cosmetic container that is operated by a silicon pump has been disclosed in Korean Patent Application Publication No. 10-2013-0115670.

According to this cosmetic container, it is possible to solve the problem by pressing a button to squeeze out a predetermined amount of makeup, but the structure is complicated and many parts are used, so it takes much time to manufacture the container. Accordingly, productivity and economy are deteriorated and convenience in use is also deteriorated.

SUMMARY OF INVENTION

Technical Problem

The present invention has been made in an effort to solve the problems and an object of the present invention is to dispense a predetermined amount of content in a container by pressing the content with a pressing-dispensing member.

Another object of the present invention is to improve productivity and convenience in use by employing a simple structure for dispensing a predetermined amount of content.

Solution to Problem

A folder type cosmetic container of the present invention includes: a tube-shaped container part having an open front end and storing content; a housing receiving and protecting the container part; and a pressing-dispensing unit pressing and dispensing the content in the container part by folding from the front end of the housing.

The housing includes: a second body receiving the container part; a first body combined with the second body and protecting the container part; and a movement guide hole formed through the first body such that a pressing-dispensing member folds and presses the container part.

The pressing-dispensing unit includes: rotation guide grooves formed on the edge of a side of the housing to face each other; a rotary lid coupled to the rotation guide grooves through rotation guide projections and opening/closing a dispensing guide when the pressing-dispensing member is moved; and a pressing-dispensing member coupled to the rotary lid and folded to press the container part.

The folder type cosmetic container further includes a pressing projection formed on a side of the pressing-dispensing member and pressing the container part.

The folder type cosmetic container further includes a pressure transmission member disposed inside the first body of the housing to transmit pressure by the pressing projection to the container part.

The folder type cosmetic container further includes fixed-quantity dispensing unit dispensing a predetermined amount of the content at the front end of the container part by being moved by pressure of the content pressured and moved by the pressing-dispensing unit.

Advantageous Effects of Invention

According to the present invention, since the content in the container part is dispensed by a predetermined amount by pressure of the pressing-dispensing member, the cosmetic container can be conveniently used while reducing waste of the content.

Further, according to the present invention, it is possible to improve productivity, reduce the manufacturing cost, and improve convenience in use by employing a simple structure for dispensing a predetermined amount of content.

DESCRIPTION OF EMBODIMENTS

Embodiments of the present invention will be described in detail with reference to the accompanying drawings so that those skilled in the art can easily achieve the present invention. However, the present invention may be modified in various different ways and is not limited to the embodiments described herein.

Figure 1:
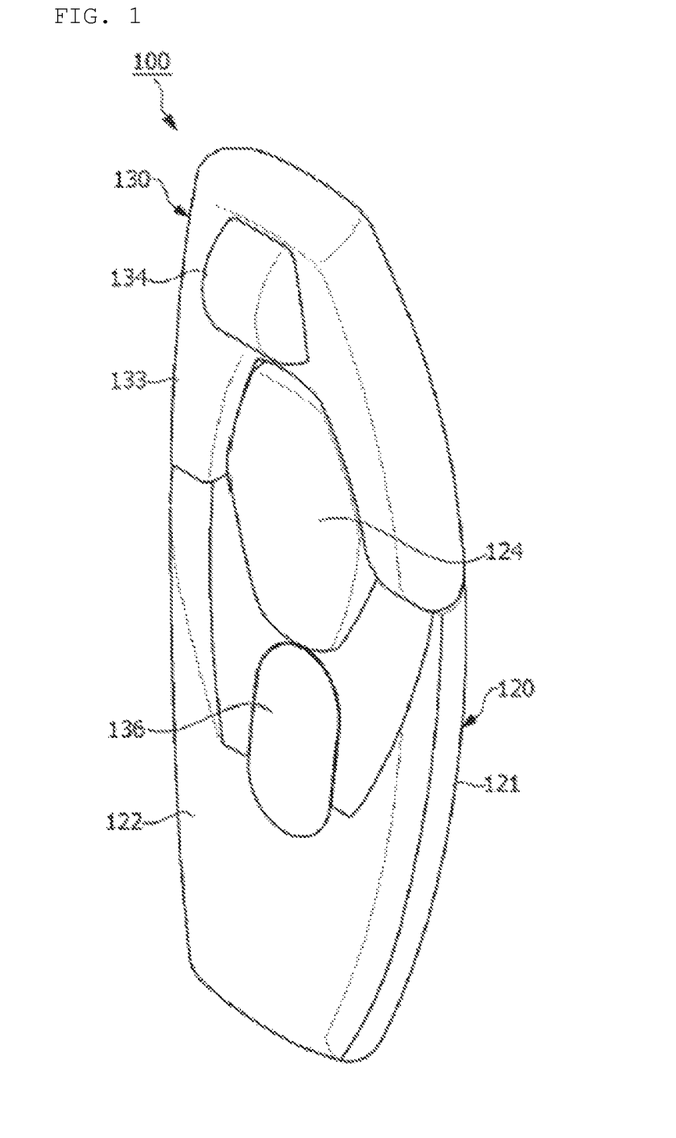
FIG. 1 is a perspective view of a folder type cosmetic container according to the present invention.
Figure 2:
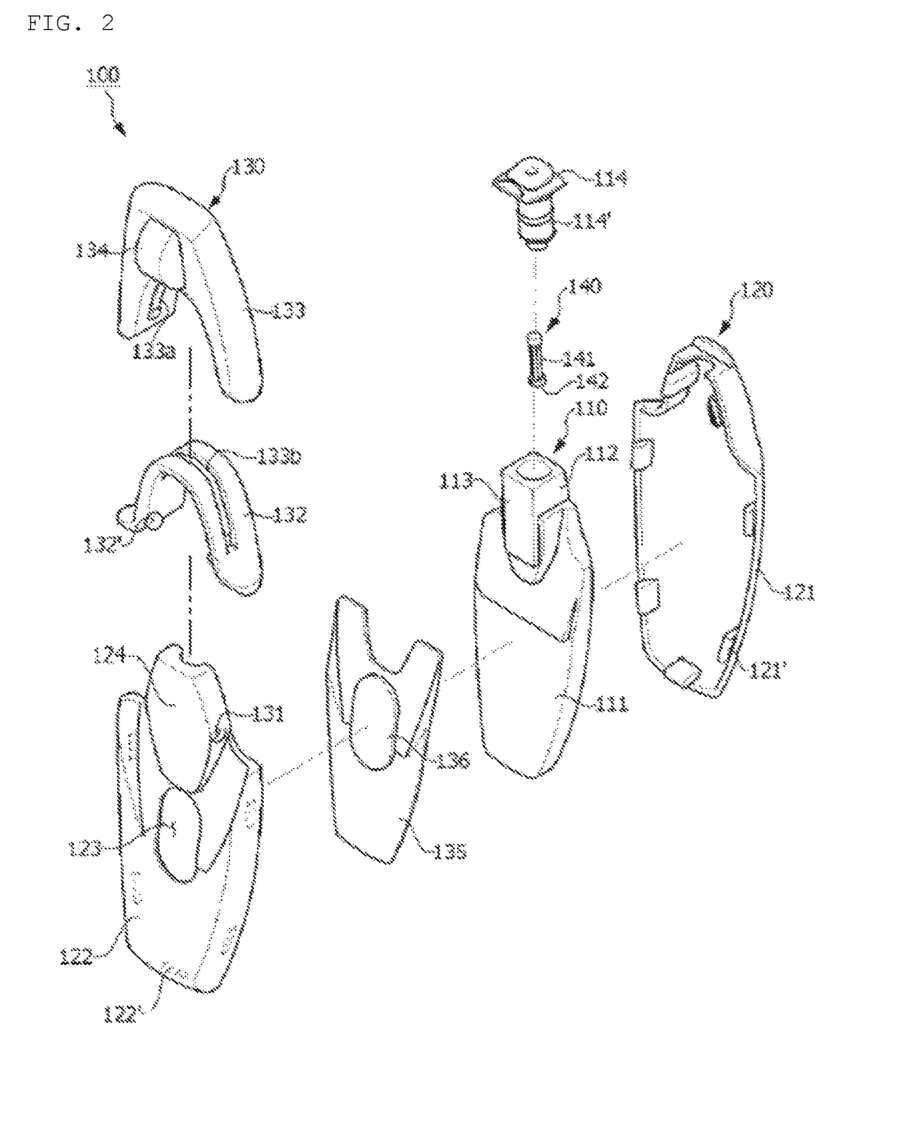
FIG. 2 is an exploded perspective view of the folder type cosmetic container according to the present invention.

FIG. 1 is a perspective view of a folder type cosmetic container according to the present invention and FIG. 2 is an exploded perspective view of the folder type cosmetic container according to the present invention.

A folder type cosmetic container 100 according to the present invention includes a container part 110, a housing 120, a pressing-dispensing unit 130.

The container part 110, which is a part for storing content, includes a container body 111 and a dispensing guide 114.

The container body 111 is open at a front end 112 and has an internal space for storing content.

The container body 111 further has a coupling member 113 protruding from a side thereof to be coupled in a coupling space of the housing 120.

The dispensing guide 114 is mounted on the front end 112 of the container body 111 to supply content into a through-hole 114' formed therein.

The housing 120, which is a part for receiving and protecting the container part 110, includes a second body 121, a first body 122, and a movement guide hole 123.

The second body 121 is recessed and receives the container part 110.

The first body 122 is combined with the second body 121 to protect the container part 110.

The movement guide hole 123 is formed through the first body 122 and guides a pressing-dispensing member 133 that folds and presses the container part 110.

The first body 122 further has a coupling space 124 coupled to the coupling member 113 of the container part 110 on a side to prevent movement.

The pressing-dispensing unit 130, which is a part for dispending content by folding from the front end of the housing 120 and pressing the content, includes rotation guide grooves 131, a rotary lid 132, and a pressing-dispensing member 133.

The rotation guide grooves 131 may be formed on the edge of a side of the housing 120 to face each other and guide the rotary lid 132 that is rotated, but they may be formed through the housing 120 to be able to guide the rotary lid 132 that is rotated.

The rotary lid 132 is coupled to the rotation guide grooves 131 through rotation guide projections 132' and opens/closes the dispensing guide 114 when the pressing-dispensing member 133 is moved.

The pressing-dispensing member 133, which is a part that is coupled to the rotary lid 132 and rotated to be folded with respect to the housing 120 to press the container part 110, has a pressing projection 134 on a side, so it can easily press the container part 110.

A pressure transmission member 135 is further disposed inside the first body 122 of the housing to uniformly transmit pressure from the pressing projection 134 to the container part 110, and a pressure transmission projection 136 protrudes from a side of the pressure transmission unit 135 and is inserted in the movement guide hole 123 of the housing 120.

A fixed-quantity dispensing unit 140 that is pressed and moved by the pressing-dispensing unit 130 and dispenses a predetermined amount of content at the front end of the container part 110 is further provided.

The fixed-quantity dispensing unit 140 includes a dispensing guide shaft 141 and dispensing control portions 142.

The dispensing guide shaft 141 has a length to be able to move in the dispensing guide member 114.

The dispensing control portions 143 protrude outward at both ends of the dispensing guide shaft 141 and guide dispensing of content by opening/closing both sides of the through-hole 114' of the dispensing guide 114.

Next, a process of assembling and using the cosmetic container having this configuration according to the present invention is described.

Figure 3:
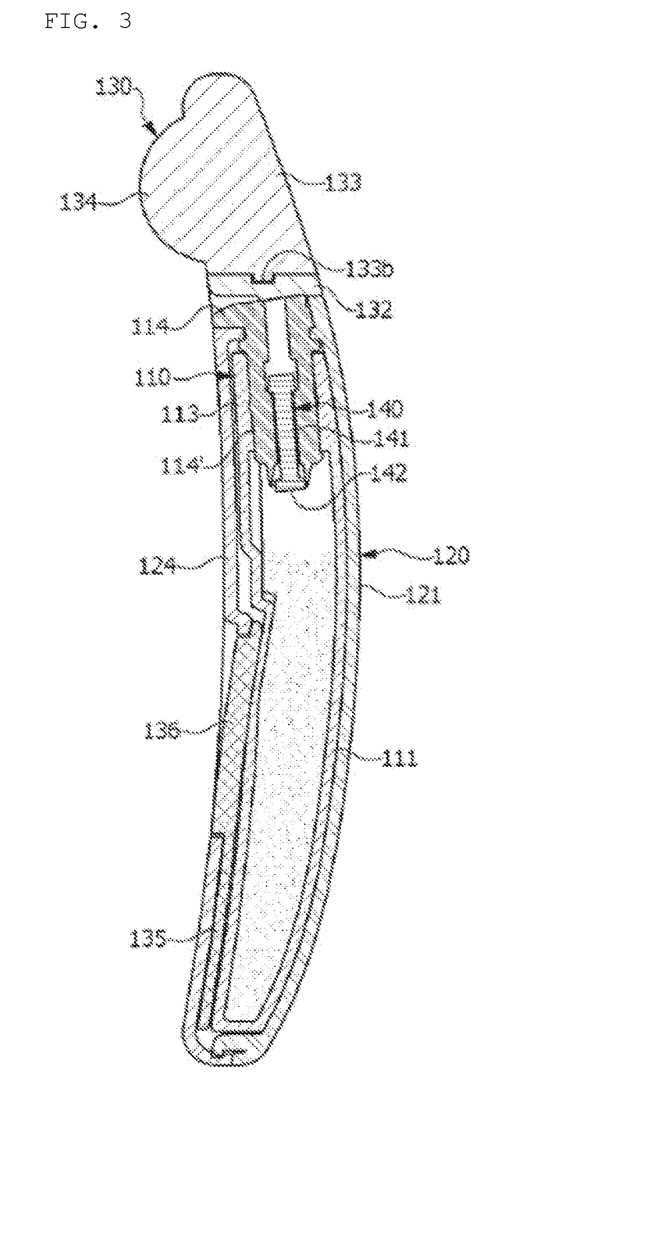
FIG. 3 is a cross-sectional view of the folder type cosmetic container according to the present invention.

First, as in FIG. 3, the fixed-quantity dispensing unit 140 having the dispensing control portions 142 protruded at both ends of the dispensing guide shaft 141 is inserted into the through-hole 114' of the dispensing guide 114. The fixed-quantity dispensing unit 140 inserted in the through-hole 114' is moved down by its own weight and the dispensing control portion 142 at the upper end of the dispensing guide shaft 141 closes the top of the through-hole 114' and the dispensing control portion 142 at the lower end of the dispensing guide shaft 141 opens the bottom of the through-hole 114'.

Further, the dispensing guide 114 combined with the fixed-quantity dispensing unit 140 is coupled to the open front end 112 of the container part 110 having a predetermined amount of content in the container body 111, whereby a sealing projection (not shown) formed on the outer side of the dispensing guide 114 is brought in close contact with the inner side of the front end 112 for firm combination, and the bottom of the upper end of the dispensing guide 114 is seated on the top of the front end 112 of the container part 110.

The container part 110 combined with the dispensing guide 114 is seated on the second body 121 of the housing 120 and then the first body 122 is coupled and fixed to the second body 121, in which elastic projections 121' formed at any one of the second body 121 and the first body 122 are fitted into projection coupling grooves 122' formed at the other body, whereby the housing 120 can protect the container part 110.

When the container part 110 is combined with the housing 120, the pressing-dispensing unit 130 is coupled to the front end of the first body 122 of the housing 120, thereby closing the through-hole 114' of the dispensing guide 114. The dispensing-pressing unit 130 is combined with the housing 120 such that the rotation guide shaft 132' of the rotary lid 132 are inserted into the rotation guide grooves 131 formed at the front end of the first body 122 of the housing 120 and the inner side of the rotary lid 132 closes the through-hole 114' of the dispensing guide 114.

Further, when the pressing-dispensing member 133 is coupled to the outer side of the rotary lid 132, assembly of the cosmetic container 100 of the present invention is finished. A projection 133a is formed on any one of the outer side of the rotary lid 132 and the inner side of the pressing-dispensing member and a groove 133b is formed on the other one. Accordingly, the projection 133a may be forcibly fitted in the groove 133b not to be separated, or a hook may be formed on the projection so that the rotary lid 132 and the pressing-dispensing member 133 are melt-bonded when the projection is fitted in the groove.

The pressing-dispensing member 133 coupled to the rotary lid 132 is in close contact with the outer side of the first body 122 of the housing 120, so it stands by the next operation without rotating.

Figure 4:
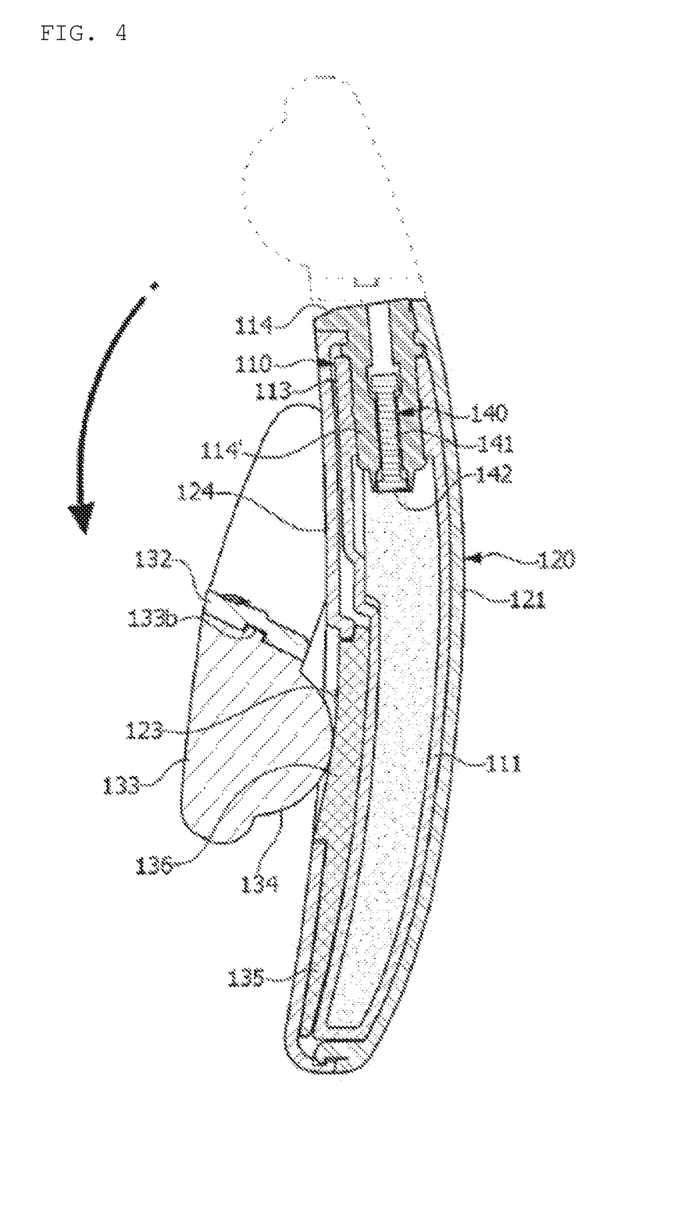
FIGS. 4 to 7 are views showing the state when the folder type cosmetic container according to the present invention is used.

In order to use the cosmetic container 100 assembled through the process described above in accordance with the present invention, as shown in FIG. 4, a user moves forward the pressing-dispensing member 133 of the pressing-dispensing unit 130.

In this process, the pressing-dispensing member 133 and the rotary lid 132 combined with the pressing-dispensing member 133 are folded and rotated forward about the rotation guide projections 132' fitted in the rotation guide grooves 131 and the rotary lid 132 is separated from the dispensing guide 114, so the dispensing guide 114 is opened.

Even with the rotary lid 132 separated from the dispensing guide 114, the rotary lid 132 is folded forward, so the pressing-dispensing member 133 is positioned ahead of the first body 122 of the housing 120 and the pressing projections 134 of the pressing-dispensing member 133 is brought in close contact with a side of the container body 111 of the container part 110 or the pressure transmission projection 136 of the pressure transmission member 135 via the movement guide hole 123 of the first body 122.

In this state, when the pressing-dispensing member 133 is pressed, the pressing projection 134 of the pressing-dispensing member 133 presses the container body 111 or the pressure transmission projection 136 of the pressing-dispensing member 135 and the content in the container body 111 is moved to the dispensing guide 114 by the pressure of the pressing projection 134. Accordingly, some of the content is dispensed to the through-hole 114' of the dispensing guide 114 and some of the content presses the dispensing control portion 142 at the lower end of the dispensing guide shaft 141 of the fixed-quantity dispensing unit 140.

The dispensing guide shaft 141 having the dispensing control portion 142 at the lower end moves out of the housing 120 along the through-hole 114' of the dispensing guide 114 and the dispending control portion 142 at the upper end of the dispensing guide shaft 141 moves to the upper end of the through-hole 114' and opens the upper end of the through-hole 114'.

A user can use the content dispensed from the front end of the container part 110 through the open through-hole 114'.

As the content at the front end of the container part 110 is dispensed, the dispensing control portion 142 closes the through-hole 114' of the dispensing guide 114 and stops the content from being dispensed, so only a predetermined amount of content can be dispensed and used.

Figure 5:
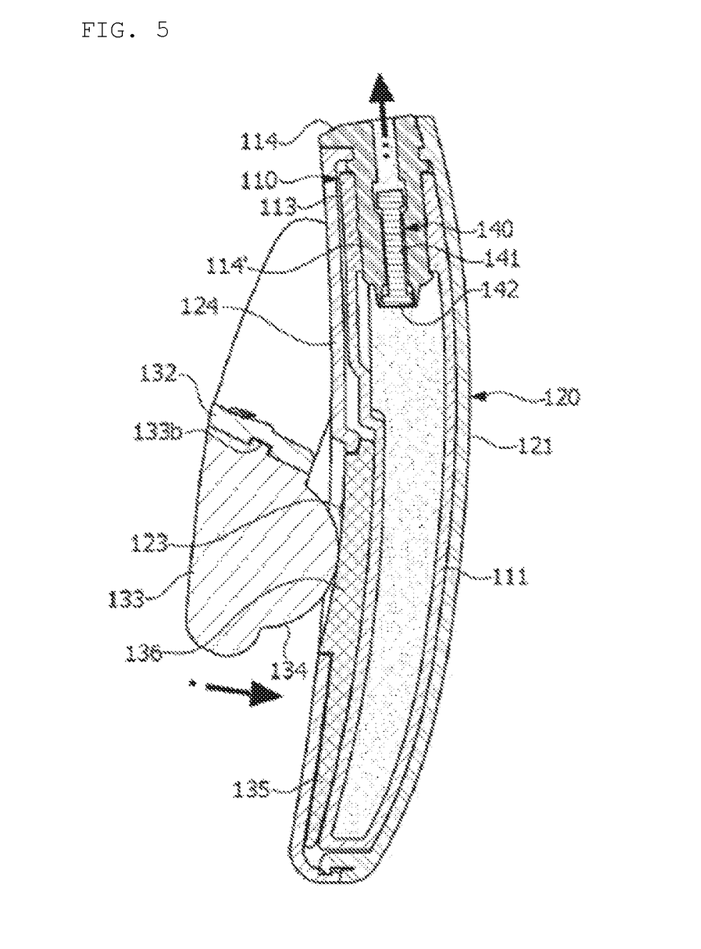
Figure 6:
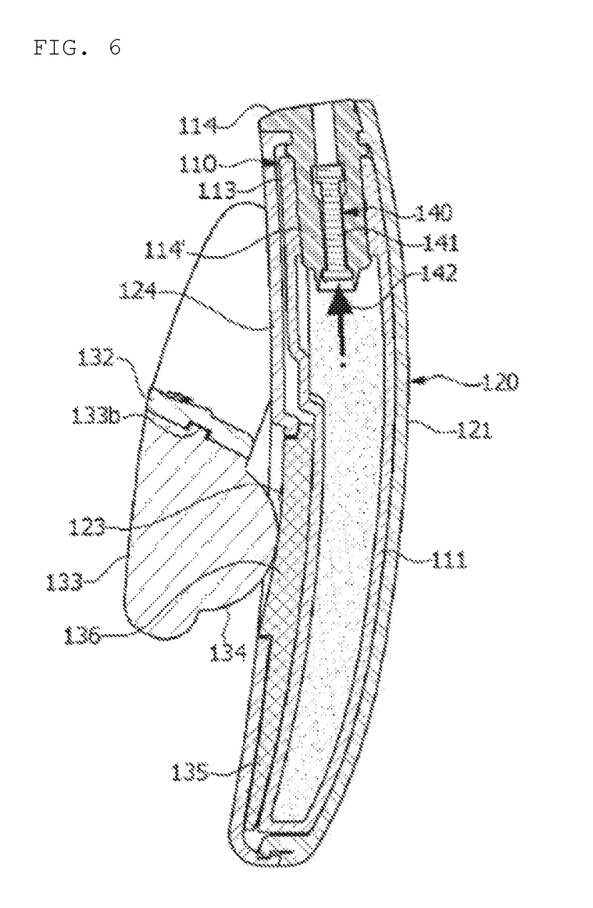

The pressure transmission member 135 is disposed inside the first body 122 of the housing 120 so that the pressing projection 134 of the pressing-dispensing member 133 can uniformly press a side of the container part 110 when it presses the container part 110, as in FIGS. 5 and 6, and is positioned at the front end of the container body 110 until the dispensing control portion 142 at the lower end closes the through-hole 114' of the dispensing guide 114, so a predetermined amount of content can be dispensed and used.

The pressure transmission member 135 may be in close contact with a side of the container part 110 so that it can transmit pressure by the pressing projection 134 to the container part 110 when it is pressed by the pressing projection 134 moving toward the movement guide hole 123.

Further, the pressure transmission member 135 is curved such that the lower end protrudes further than the upper end to be able to press the container part 110 from the lower end of the container part. When the pressure by the pressing projection 134 is removed, the pressure guide projection 136 formed on a side of the pressure transmission member 135 is inserted into the movement guide hole 123 and can prevent movement of the pressure transmission member 135.

Figure 7:
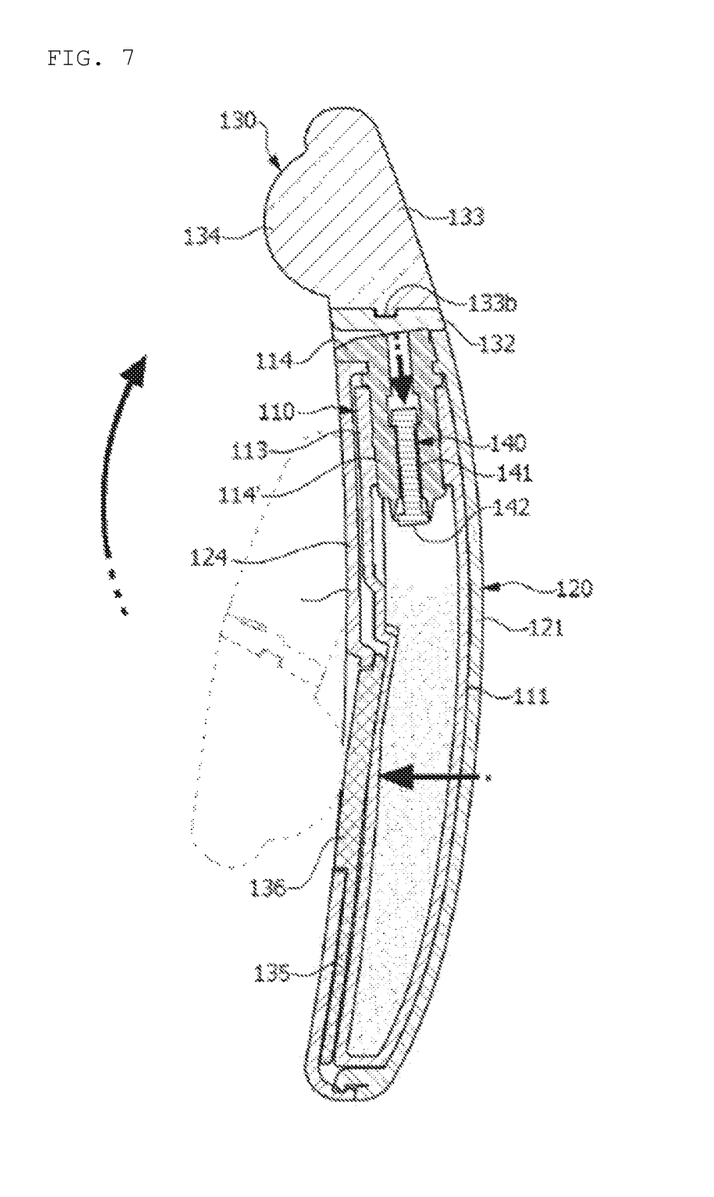

When the pressure of the container part 110 is removed after the predetermined amount of content dispensed to the dispensing guide member 114 through the process described above is used, the container part 110 is returned and the dispensing guide shaft 141 of the fixed-quantity dispensing unit 140 is moved down by the returning force of the container part 110 and the dispensing control portion 142 at the lower end of the dispensing guide shaft 141 opens the lower end of the through-hole 114' and closes the upper portion of the dispensing control portion 142 at the upper end.

In this state, when the pressing-dispensing member 133 of the pressing-dispensing unit 130 is unfolded in the opposite direction to the folding direction, the pressing-dispensing member 133 and the rotary lid 132 coupled to the pressing-dispensing member 133 are rotated rearward about the rotation guide shafts 132' inserted in the rotary guide grooves 131, the rotary lid 132 closes the through-hole 114' of the dispending guide 114, and the pressing-dispensing member 133 comes in close contact with the first body 122 of the housing 120 and stands by the next operation.

Although the present invention was described above through a limited embodiment with reference to the drawings, the present invention is not limited thereto and may be changed and modified in various ways from the specification by those skilled in the art.

Therefore, the scope of the present invention should not be limited to the embodiment(s), but should be determined by not only the following claims, but equivalents of the claims.

BEST MODE FOR INVENTION

Mode for invention was described with the best mode for invention.

INDUSTRIAL APPLICABILITY

The present invention relates to a folder type cosmetic container, which can be applied to various cosmetic containers and can be repeatedly used, thereby having an industrial applicability.

The invention claimed is:
1. A folder type cosmetic container, comprising:
a container part having an open front end and configured to store a content;
a housing configured to accommodate the container part;
a pressing-dispensing assembly configured to dispense the content in the container part by pivoting adjacent the front end of the housing and pressing the container part; and
a fixed-quantity dispensing assembly configured to dispense a predetermined amount of the content at the front end of the container part by being moved by pressure of the content pressured and moved by the pressing-dispensing assembly,
wherein the fixed-quantity dispensing assembly includes:
a dispensing guide shaft; and
a dispensing control portion protruding from an end of the dispensing guide shaft to guide the content that is dispensed.
2. The folder type cosmetic container of claim 1, wherein the housing includes:
a first body; and
a second body coupled with the first body to accommodate the container part; and
a movement guide hole disposed on the first body.
3. The folder type cosmetic container of claim 1, wherein the pressing-dispensing assembly comprises:
a pair of rotation guide grooves disposed on side surfaces of the housing to face each other;
a rotary lid coupled to the pair of rotation guide grooves through rotation guide projections and configured to open or close a dispensing guide according to a movement of the pressing-dispensing member; and
a pressing-dispensing member coupled to the rotary lid and configured to rotate with respect to the housing to press the container part.
4. The folder type cosmetic container of claim 3, further comprising a pressing projection protruding from a side of the pressing-dispensing member to press the container part.
5. The folder type cosmetic container of claim 4, further comprising a pressure transmission member disposed inside the first body of the housing to transmit pressure applied by the pressing projection to the container part.
6. A folder type cosmetic container, comprising:
a container part having an open front end and configured to store a content;
a housing configured to accommodate the container part;
a pressing-dispensing assembly configured to dispense the content in the container part by pivoting adjacent the front end of the housing and pressing the container part; and a fixed-quantity dispensing assembly configured to dispense a predetermined amount of the content at the front end of the container part by being moved by pressure of the content pressured and moved by the pressing-dispensing assembly, wherein a pressing projection is formed to protrude from a side of the pressing-dispensing assembly to apply pressure to a side of the container part in a direction of a pivoting movement of the pressure-dispensing assembly.

7. The folder type cosmetic container of claim 6, wherein the housing includes:

a first body; and a second body coupled with the first body to accommodate the container part; and a movement guide hole disposed on the first body.

8. The folder type cosmetic container of claim 6, wherein the pressing-dispensing assembly comprises:

a pair of rotation guide grooves disposed on side surfaces of the housing to face each other;

a rotary lid coupled to the pair of rotation guide grooves through rotation guide projections and configured to open or close a dispensing guide according to a movement of the pressing-dispensing member; and a pressing-dispensing member coupled to the rotary lid and configured to rotate with respect to the housing to press the container part.

9. The folder type cosmetic container of claim 6, further comprising a pressure transmission member disposed inside the first body of the housing to transmit pressure applied by the pressing projection to the container part.

10. The folder type cosmetic container of claim 6, wherein the fixed-quantity dispensing assembly includes:

a dispensing guide shaft; and a dispensing control portion protruding from an end of the dispensing guide shaft to guide the content that is dispensed.

* * * * *